(12) United States Patent
Ross et al.

(10) Patent No.: US 12,186,258 B2
(45) Date of Patent: Jan. 7, 2025

(54) ORTHOPAEDIC EXTERNAL FIXATION SYSTEM WITH REMOVABLE RAILS OR SKATES

(71) Applicants: Orthofix S.R.L., Verona (IT); Texas Scottish Rite Hospital for Children, Dallas, TX (US)

(72) Inventors: John D. Ross, Ovilla, TX (US); Mikhail L. Samchukov, Coppell, TX (US); Alexander M. Cherkashin, Flower Mound, TX (US); Karen D. Standefer, Flower Mound, TX (US); Daniele Venturini, Povegliano Veronese (IT); Mario Donnici, Bussolengo (IT); Andrea Ottoboni, Giacciano con Baruchella (IT)

(73) Assignees: Orthofix SRL, Bussolengo (IT); Texas Scottish Rite Hospital for Children, Dallas, TX (US)

( * ) Notice: Subject to any disclaimer, the term of this patent is extended or adjusted under 35 U.S.C. 154(b) by 893 days.

(21) Appl. No.: 17/103,052

(22) Filed: Nov. 24, 2020

(65) Prior Publication Data
US 2022/0160572 A1    May 26, 2022

(51) Int. Cl.
*A61B 17/62* (2006.01)
*A61B 17/64* (2006.01)
(Continued)

(52) U.S. Cl.
CPC ............. *A61H 3/00* (2013.01); *A61B 17/62* (2013.01); *A61B 17/645* (2013.01); *A61B 2017/00017* (2013.01); *A61B 2017/00075* (2013.01); *A61B 2017/00119* (2013.01); *A61B 2017/00221* (2013.01); *A61B 2017/00477* (2013.01); *A61H 2003/007* (2013.01); *A61H 2201/1253* (2013.01); *A61H 2201/5007* (2013.01); *A61H 2201/5043* (2013.01); *A61H 2201/5048* (2013.01); *A61H 2201/5064* (2013.01); *A61H 2201/5071* (2013.01);
(Continued)

(58) Field of Classification Search
CPC .................. A61B 17/60–66; A61H 2201/5064
See application file for complete search history.

(56) References Cited

U.S. PATENT DOCUMENTS 6,174,294 B1 * 1/2001 Crabb .................. A61B 5/1036
                                                600/595
9,311,827 B1 * 4/2016 Alqahtani ................ A43B 3/34
(Continued)

*Primary Examiner* — Eduardo C Robert
*Assistant Examiner* — Steven J Cotroneo
(74) *Attorney, Agent, or Firm* — Haynes and Boone, LLP

(57) ABSTRACT

An improved orthopaedic external fixation system with removable rails or skates and may include: at least a distal foot fixation element; at least a pair of rails or skates removably connected to the foot fixation element; at least a load sensor associated to at least one of the rails or skates; an electronic apparatus coupled to the load sensor and receiving an electric signal from the load sensor; an electronic controller coupled to the apparatus and issuing at least a flag signal upon detection of a threshold pressure force on said at least one of said rails or skates. This electronic controller may be mounted on the orthopaedic system or may be a structurally independent host device including a controller that is in signal communication with the load sensors.

16 Claims, 12 Drawing Sheets

(51) Int. Cl.
*A61H 3/00* (2006.01)
*A61B 17/00* (2006.01)

(52) U.S. Cl.
CPC ............... *A61H 2201/5097* (2013.01); *A61H 2205/106* (2013.01); *A61H 2205/12* (2013.01)

(56) References Cited

U.S. PATENT DOCUMENTS

| | | | |
|---|---|---|---|
| 9,568,381 B2* | 2/2017 | Daniecki | A61B 5/6807 |
| 10,070,680 B2* | 9/2018 | Molyneux | A43B 3/34 |
| 11,197,692 B2* | 12/2021 | Gurevich | A61B 17/6425 |
| 2013/0000156 A1* | 1/2013 | Andoh | A43B 3/34 |
| | | | 36/136 |
| 2013/0204248 A1* | 8/2013 | Singh | A61B 17/645 |
| | | | 606/56 |
| 2016/0256194 A1* | 9/2016 | Wong | A61B 17/8866 |
| 2017/0154514 A1* | 6/2017 | Condon | G08B 21/0288 |
| 2018/0110672 A1* | 4/2018 | Kasravi | A01K 27/008 |
| 2018/0310962 A1* | 11/2018 | Ottoboni | A61B 17/6425 |
| 2019/0021894 A1* | 1/2019 | Zelen | A61B 17/62 |
| 2021/0022666 A1* | 1/2021 | Malawey | A43B 17/006 |
| 2021/0027879 A1* | 1/2021 | Noblett | A61B 17/66 |
| 2021/0338517 A1* | 11/2021 | Taniguchi | A61H 3/061 |
| 2022/0354539 A1* | 11/2022 | Ferrante | A61B 17/62 |
| 2023/0074130 A1* | 3/2023 | Sun | A61B 17/62 |
| 2023/0248393 A1* | 8/2023 | Cheng | A61B 17/66 |
| | | | 606/56 |

* cited by examiner

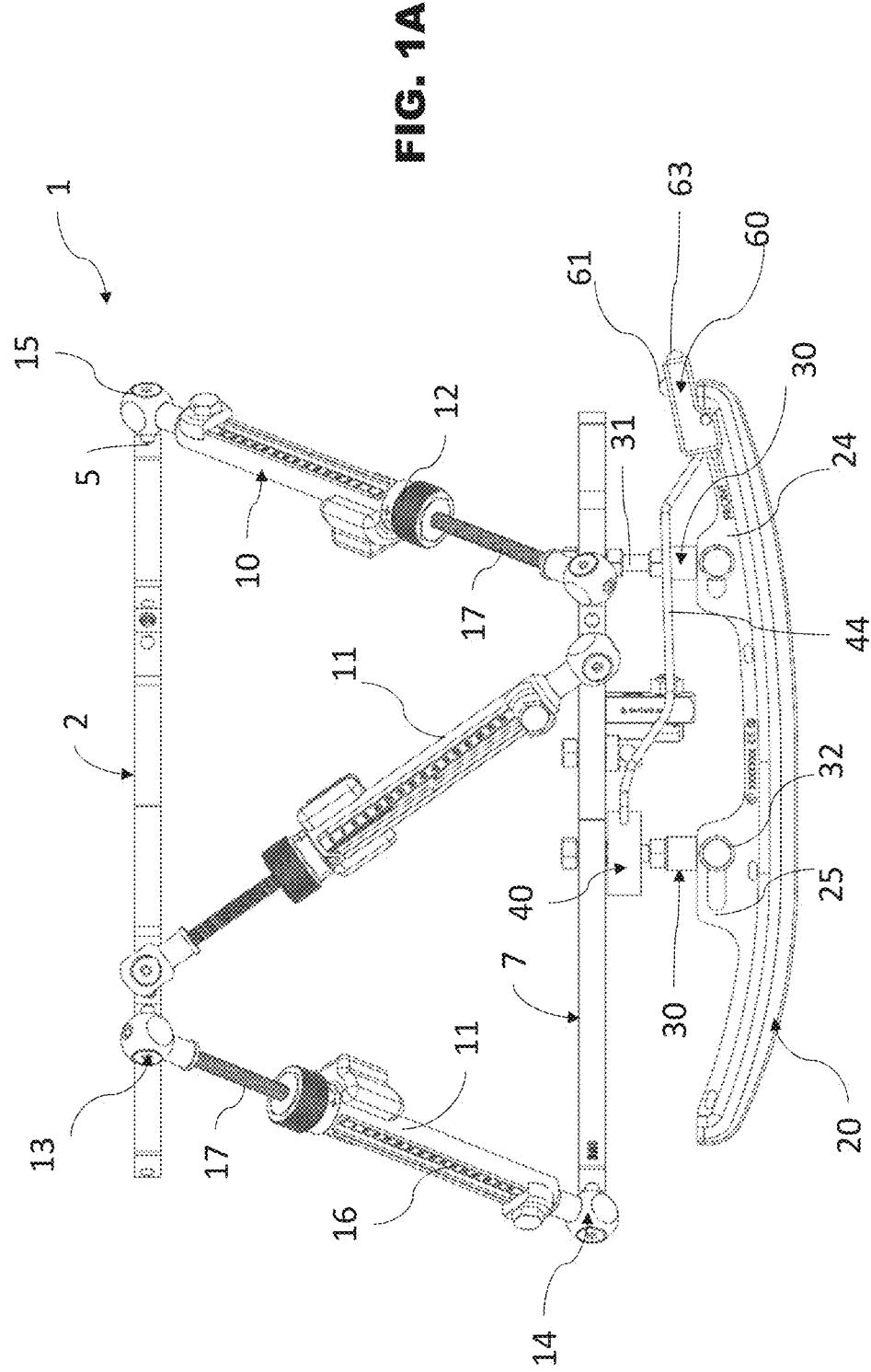

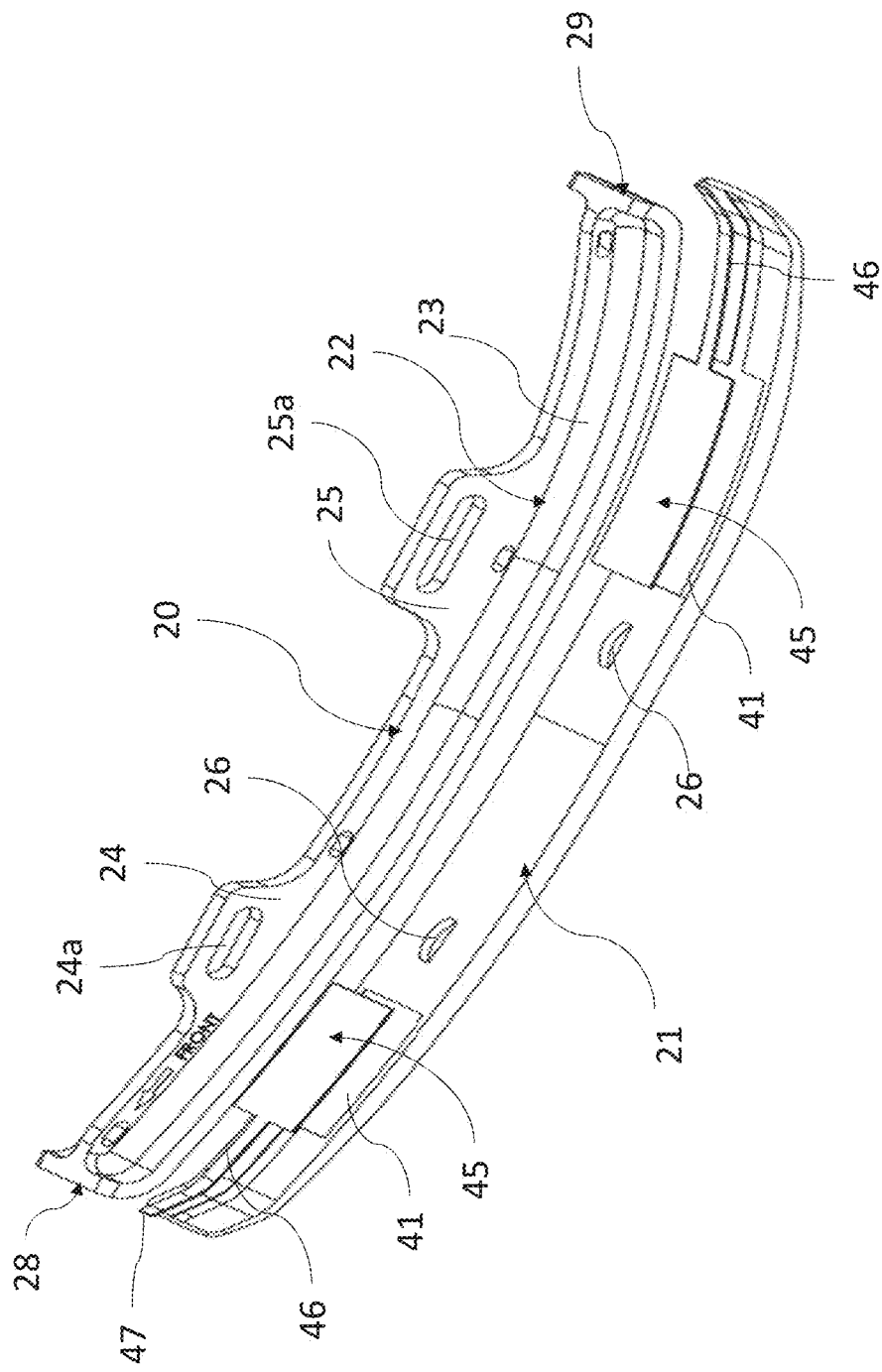

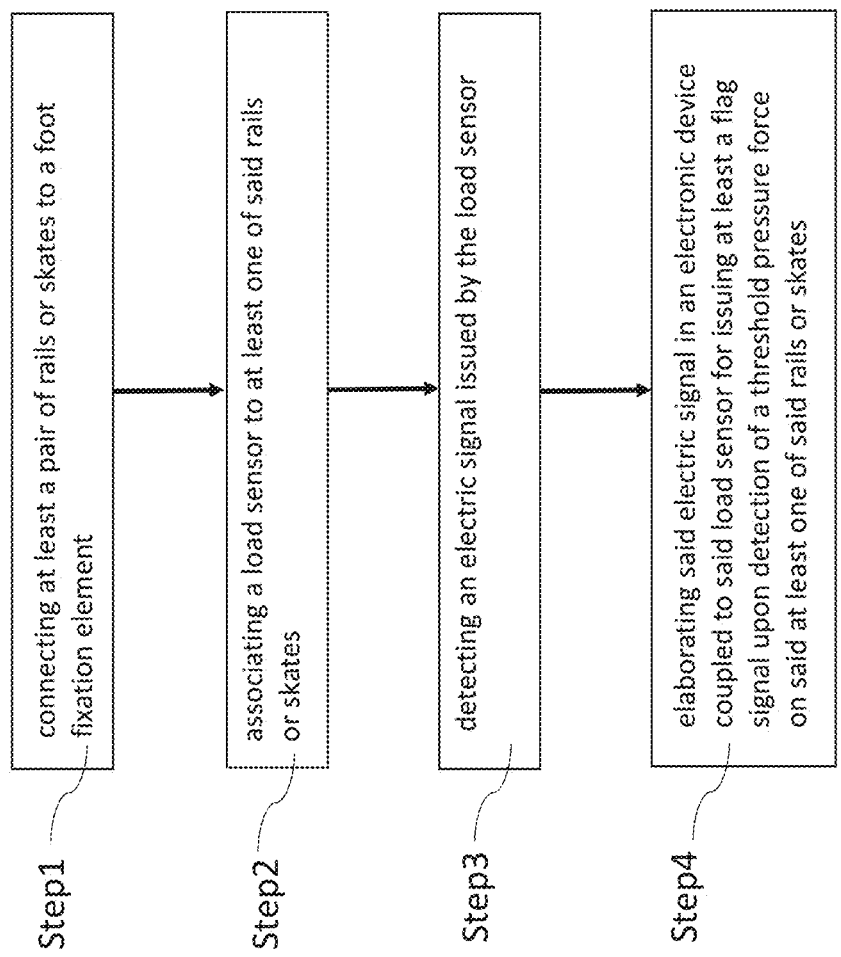

ORTHOPAEDIC EXTERNAL FIXATION SYSTEM WITH REMOVABLE RAILS OR SKATES

TECHNICAL FIELD

The present invention is applicable to the sector of orthopaedic and relates to an improved orthopaedic external fixation system equipped with removeable rails or skates allowing the patient to walk without abutting his/her foot on the walking surface in the ground.

According to the present disclosure, the above system has been improved by the adoption of an accessory that allows the patient and the surgeon to measure the amount of load transferred to the leg.

BACKGROUND OF THE DISCLOSURE

As it is well known in this specific technical field, external fixation systems are frequently used for a fast recovering of serious fractures and limb reconstructions involving the lower extremity and more specifically: the foot, the ankle, the proximal or distal tibia or even the knee.

External fixation systems of this kind are structured with circular or semi-circular external supports statically interconnected by threaded or telescopic rods or hinged between those circular or semi-circular elements.

Moreover, in order to allow the patients to whom an external fixation system has been attached to be movable during treatment, fixed or adjustable rails or walking skates are associated underneath a distal semi-circular external support, namely a U-shaped foot plate, attached to the foot. Such rails or skates allow the patient to walk normally without however directly touching the walking surface on the ground by the foot.

For instance, the U.S. Pat. No. 10,743,917 assigned to the same Applicant discloses an external fixation system using such kind of rails or skates that are removably associated to the foot external support.

One problem, which may arise with these orthopaedic fixation systems, is just given by the possibility offered to the patient to walk without providing control on the limb loading during walking as well as preventing overlapping with surrounded objects.

For example, the load exerted on the low-density osteopenic foot bones and pathological adjacent joints may be too excessive and not in compliance with a therapeutic protocol administered by the surgeon in the post-operative period. In contrast, patient is often obligated to walk with partial or full weight bearing for faster fracture/osteotomy healing and new bone remodeling but unable to control amount of loading during walking or count the number of steps with the certain prescribed amount of load.

Some partial solutions have already been proposed to solve this drawback. For instance, an old U.S. Pat. No. 3,791,375 provides a sort of shoe for limiting the application of weight on a lower extremity, usually during recovery from orthopedic surgery on the lower extremity. A sensor is applied to the sole of the shoe and a warning signal is generated in case of excessive ambulation force to advice the patient to be more careful.

However, this solution was not proposed for cases with an external fixator and cannot be applied to the system of the present disclosure.

A further prior art solution is disclosed in the European Patent No. EP 2 762 065 A1 concerning systems, devices, and methods for providing user feedback regarding compliance with a preset partial weight bearing.

Even in this case, a sort of boot is provided for a patient that is recovering from orthopedic surgery on a lower extremity. A computer system receives force data from a non-compressible force transmitter that is incorporated into the boot and determines whether the user is within a predefined pressure compliance range.

As in the previous solution, this second prior art disclosure is not applicable to the external fixation system of the present application since the patient bearing an external fixation system on the foot and ankle cannot wear a shoe or a boot.

What is more, in the external fixation system of the present disclosure, there is no sole and the foot of the patient is not in direct contact with the ground's walking surface.

Another problem which may arise with existing orthopaedic fixation systems is an additional bulkiness of the external frame, potentially leading to interference (impact) with surrounding objects such as walls, chairs, and steps, especially in the dark. This is especially important for patients with significantly reduce or completely loss sensitivity of the foot, e.g., patients with Charcot disease The aim of the present disclosure is that of providing an improved orthopaedic external fixation system with removable rails or skates having structural and functional features allowing to monitor the load exerted by the patient on the limb during walking and to provide a feedback to the patient and/or the surgeon in order to ensure compliance with a therapeutic protocol administered by the surgeon in the post-operative period.

A further aim of the present disclosure is that of providing an improved orthopaedic external fixation system with removable rails or skates having a simple and practical configuration allowing to monitor the load exerted by the patient in a very precise and reliable manner and/or monitoring the dynamics of leg loading and preventing interference with surrounded objects while walking.

Another aim of the present disclosure is that of providing a system including monitoring features that may be attached to or removed from the orthopaedic system in an easy and timely manner also for less experienced persons, within the framework of a simple and rational constructional solution.

Another aim of the present disclosure is that of providing an improved orthopaedic external fixation system with removable rails or skates having censoring features allowing to measure distance to surrounding object and, thereby, prevent interference with those objects while walking.

SUMMARY OF THE INVENTION

The above aims are achieved by an orthopaedic external fixation system with removable rails or skates and comprising:
- at least a distal foot fixation element;
- at least a pair of rails or skates removably connected to said foot fixation element;
- at least a load sensor associated to at least one of said rails or skates;
- an electronic apparatus coupled to the load sensor and receiving an electric signal from the load sensor;
- an electronic controller coupled to said apparatus and issuing at least a flag signal upon detection of a threshold pressure force on said at least one of load sensors of said rails or skates.

A further embodiment of the present disclosure relates to an accessory device for an orthopaedic external fixation system including at least a distal foot fixation element equipped with removeable rails or skates, said device comprising:
  at least a load sensor associated to at least one of said rails or skates;
  an electronic apparatus coupled to the load sensor and receiving an electric signal from the load sensor;
  an electronic controller coupled to said apparatus and issuing at least a flag signal upon detection of a threshold pressure force on said at least one of load sensors of said rails or skates.

Another embodiment of the present disclosure relates to a method for monitoring the pressure force exerted on a foot or a limb of a patient threated with an orthopaedic external fixation system with removable rails or skates and comprising the steps of:
  connecting at least a pair of rails or skates to a foot fixation element;
  associating a load sensor to at least one of said rails or skates;
  detecting an electric signal issued by the load sensor;
  elaborating said electric signal in an electronic controller coupled to said load sensor for issuing at least a flag signal upon detection of a threshold pressure force on said at least one of load sensors of said rails or skates.

The enclosed dependent claims describe preferred and particularly advantageous embodiments, in accordance with the present invention.

Further features and advantages will emerge from the detailed description provided hereinbelow of a preferred, but not exclusive embodiment of the present invention, with reference to the attached figures, provided by way of a non-limiting example.

BRIEF DESCRIPTION OF THE DRAWINGS

FIG. 1A shows a schematic and lateral view of the fixation system of FIG. 1;
FIG. 2 shows a schematic and perspective view of a skate configured to be associated to the fixation system of the present disclosure;
FIG. 7 shows in a block diagram the steps of a method for monitoring the pressure force exerted on a foot or a limb of a patient according to embodiments of the present disclosure.

DETAILED DESCRIPTION

Figure 1:
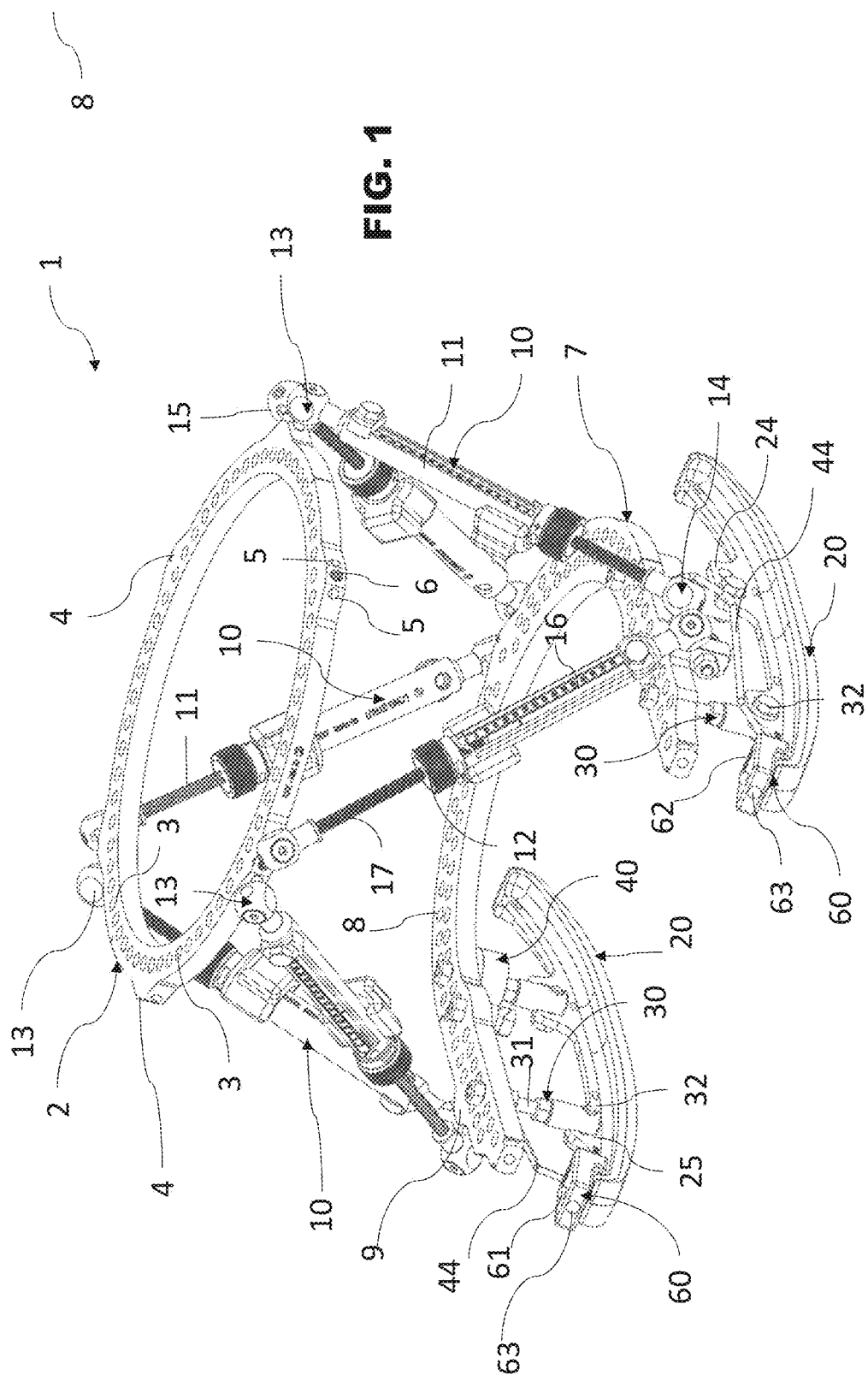
FIG. 1 shows a schematic and perspective view of an improved orthopaedic external fixation system equipped with removeable rails or skates in accordance with the present disclosure.

With reference to the enclosed figures, and in particular to the example of FIG. 1, an improved orthopaedic external fixation system with removable rails or skates is disclosed.

It is worth noting that the figures represent schematic views and are not drawn to scale, but instead they are drawn so as to emphasize the important features of the disclosure. Moreover, in the figures, the different elements are depicted in a schematic manner, their shape varying depending on the application desired. It is also noted that in the figures the same reference numbers refer to elements that are identical in shape or function. Finally, specific features described in relation to an embodiment illustrated in a figure are also applicable to the other embodiments illustrated in the other figures.

Without limiting the scope of the present disclosure, the system of FIG. 1 is globally and schematically indicated with the reference number 1 and may be considered part of the wide family of external fixation devices. Generally, external fixation devices are commonly used on both the upper and lower limbs for both adults and children in a variety of surgical procedures including limb lengthening, deformity correction and treatment of fractures, mal-unions, non-unions and bone defects.

One common external fixation device is known as Taylor Spatial Frame that is a hexapod type of device comprising at least two external fixator rings attached to bone segments by wires or half pins and connected together by six interconnecting struts that may be lengthened or shortened as necessary. Adjustment of strut lengths allows spatial manipulation of the bone segments in all the allowed six degrees of freedom (e.g., lengthening/shortening, external/internal rotation, anterior/posterior horizontal translation, medial/lateral horizontal translation, anterior/posterior angular translation, and medial/lateral angular translation) to correct linear, angular and rotational deformities simultaneously.

The system 1 of the present disclosure may be considered a hexapod type of device but the structure and configuration of the rings and the struts may even be similar to a Taylor Spatial Frame even if a TL-Hex hexapod frame is the preferred solution for adopting the improvement of the present disclosure.

First of all, the system 1 includes at least a proximal ring 2 realized from a suitably strong and rigid material such as a metal, metal alloy, plastic, composite, or ceramic. The body portion of the ring includes substantially equally spaced apertures or holes 3 positioned arcuately therein and extending through an upper ring surface to a lower ring surface.

Moreover, the ring 2 comprises substantially equally spaced angled flanges 4 extending radially from the outer surface of the ring and provided with two accessible lateral apertures 5 and central aperture 6 on their outer surface.

During an operation, the arcuately positioned holes 3 are used to connect wires and half pins inserted to the bone segments while angled flanges 4 and the accessible lateral apertures 5 are used for attachment of ball joints of the connection struts 10 and locking them in place by a conventional set screw of the central aperture 6 (not visible).

The apertures 5 are positioned obliquely in the angled flange 4 to provide the optimal range of motion for the strut 10 when connected to the fixator ring 2. In addition, struts 10 can be connected to other accessible lateral apertures 5 on outer surfaces of the ring 2.

Although the shape of the fixator ring or rings 2 is substantially circular, it is to be appreciated that the shape of this fixator external supports can vary to accommodate the physical contour of various body parts to which the fixation system 1 would be attached. For example, the fixator external supports can be configured to have an oval shape, D-shape, U-shape, C-shape, or other irregular shapes without departing from the principle of the present disclosure. In some exemplary embodiments, an elliptical fixator ring (not shown) may be particularly advantageous.

Moreover, the fixator external supports or rings 2 may be a complete circle (full ring) or a segment or portion of a circle (e.g., half ring, ⅓ ring, ¼ ring, ⅝ ring and other) that is either used alone or joined with other segments or portions of the ring to form a complete ring (not shown). In any case, a skilled in this art understands that a circular or semi-circular foot fixation element may include one of the above-mentioned portions of a circle.

The system 1 of the present disclosure includes at least a distal semi-circular external support or U-shaped foot plate 7 as a foot fixation element. We will later identify as front of the fixation system 1 the portion of the fixator located opposite to the curvature of the U-shaped portion.

This distal foot plate 7 includes a plurality of equally spaced apertures or holes 8 positioned arcuately therein and extending through an upper foot plate surface to a lower foot plate surface.

Moreover, the foot plate 7 comprises spaced angled flanges 9 extending radially from the outer surface of the foot plate and provided with an accessible aperture on their outer surface. As for the ring 2, even for the foot plate 7 the arcuately positioned holes 8 are used to connect wires and half pins inserted to the bone segments while angled flanges 9 with their accessible apertures are used for attachment of connection struts 10.

The ring 2 and the foot plate 7 are interconnected as shown in FIG. 1 through a plurality of connection struts 10, for instance six struts 10 to form a hexapod type fixation configuration.

The fixator rings 2 and the foot plate 7 may be constructed of any material that provides the structural rigidity necessary for fixation such as metal, metal alloy, carbon fibers, plastic, ceramic and so forth.

A skilled in this art will readily understand that numerous connection struts 10 may be attached at various positions about the external fixator rings 2 and 7. The angle of each the connection struts 10 relative to the proximal external fixator ring 2 and the distal external fixator half-ring 7 may be varied; even the length of the connection struts 10 may be varied and adjusted.

The connection strut 10 includes opposite ball joints 13 and 14 that can be attached to the outer surface of a proximal fixation ring 2 or a distal foot plate 7. More particularly, these joints 13, 14 are structured with a ball stud 15 attached to the aperture 5 of the flange 4.

According to embodiments of the present disclosure, a connection strut 10 of the system 1 is configured with a telescopic outer housing 11 and inner tube with a threaded rod 17 that allows for rapid adjustment in length. Gradual strut length adjustment is achieved by rotating a distraction knob 12, which is provided for advancing or reducing the length of the threaded rod 17.

In embodiments of the present disclosure the strut housing 11 may have graduation marks 16 indicating the lengths of the strut 10 as a relative value. The graduation marks 16 do not necessarily have to indicate the effective length of the strut 10 but could indicate the remaining length of the threaded rod for gradual strut length adjustment.

The orthopaedic external fixation system 1 of the present disclosure is further equipped with removeable rails or skates 20 allowing the patient to walk without abutting his/her foot on the walking surface on the ground.

Since these rail or skates 20 are identical to each other only one of them will be described in detail later with reference to the example of FIG. 2.

In accordance with the present disclosure, the system 1 further comprises connecting members 30 having a first end configured to be connected to an aperture in the distal foot plate 7 and a second end connected to a corresponding flange 24 or 25 of the skate 20.

This connecting member 30 comprises a cylindrical body 31 extending along an axis that is substantially perpendicular to the skate 20 and has a through hole arranged transversely with respect to the extension axis of the cylindrical body 31 so as to be able to receive a bolt 32 for fixing to the skate 20.

The cylindrical body 31 has a flat recessed portion around the hole so as to create a flat wall abutting against one of the flanges 24, 25.

The cylindrical body 31 has a blind threaded hole (not shown) at its opposite end to receive a fixing threaded rod for coupling to an aperture 8 of the foot plate 7 of the external fixation system 1.

Figure 6:
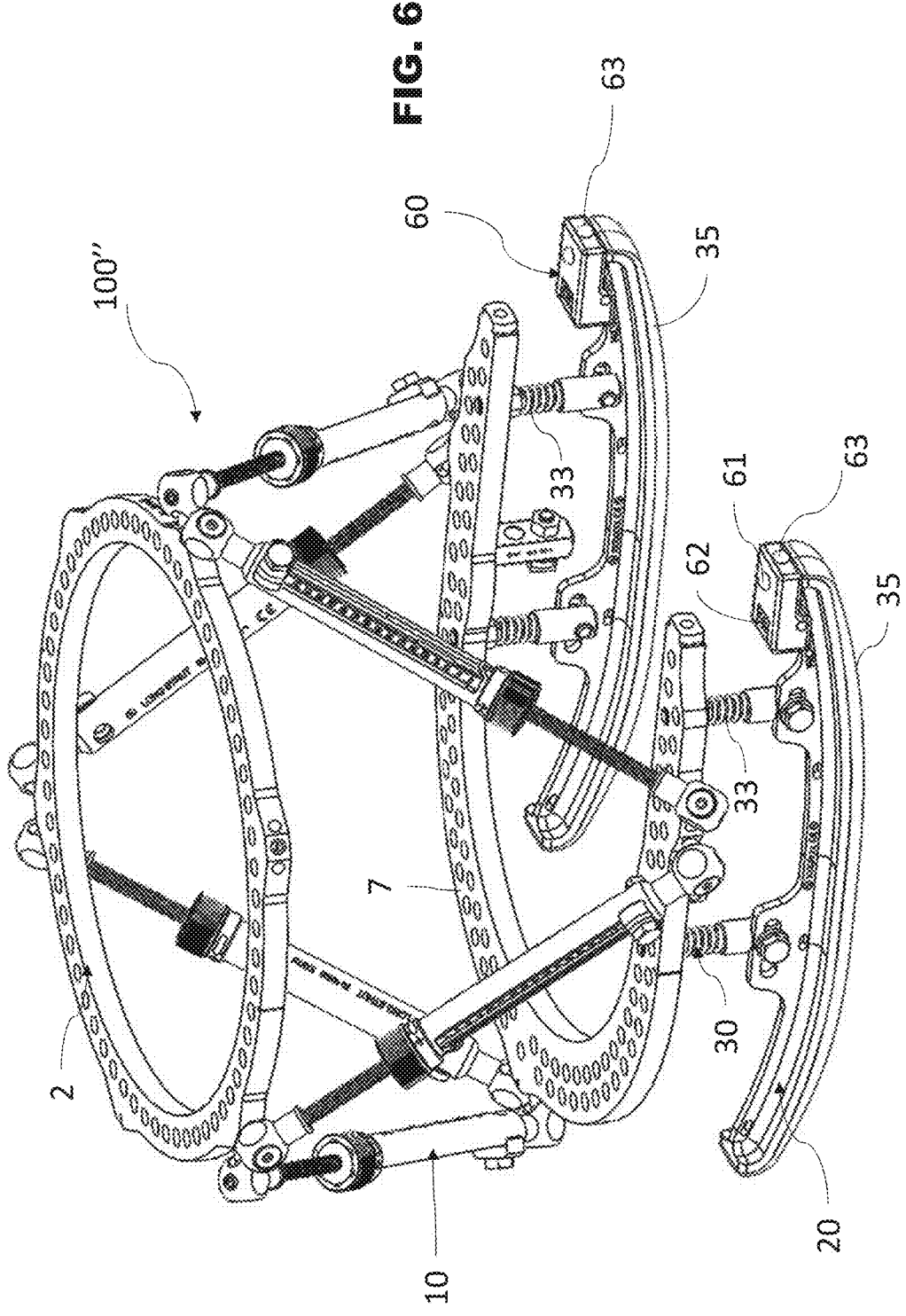
FIG. 6 shows a schematic and perspective view of another alternative embodiment of fixation system of FIG. 5.

As a possible alternative, the cylindrical body 31 may also be structured like a shock absorber and be equipped with a central dumping spring 33, for instance as shown in FIG. 6. However, a shock absorbent spring might affect loading measurements and care should be taken to adopt springs of known and very accurate elasticity properties.

According to embodiments of the present disclosure the orthopaedic system 1 includes at least a load sensor 40 associated to at least one of said rails or skates 20. The load sensor 40 may include load cells as sensitive elements as disclosed later in more detail. As an alternative, a different mechanisms of load measurement may be employed, for instance, a mechanism including strain gages or similar sensitive elements, etc.

Preferably, but not necessarily, a load sensor 40 is associated to connecting member 30 linking the foot plate 7 to the corresponding skates 20. In the example of FIGS. 1 and 1A it is shown a load sensor 40 associated to a connecting member 30 of the rear protruding portions 25, that is to say the portion closer to the back end of the skate 20.

In embodiments of the present disclosure the load sensor 40 may be coupled or associated to the skates 20 through a removable support.

In this respect, the load sensor 40 and its support may be considered an accessory device to be associated to an existing orthopaedic external fixation system equipped with removeable rails or skates to provide the same advantages of the present disclosure.

So, a rail or skate 20 equipped with the load sensor 40 may be considered a sensorized rail capable to detect a pressure force exerted on the foot or the limb.

In the example of FIG. 1 it is also shown an envelope box 60 that may include and protect an electronic apparatus 70 cooperating with the fixation system 1 and that will be disclosed later. The envelope box 60 further includes a LED flag 61 and a speaker 62. A proximity sensor 63 is also provided on the front portion of the envelope box 60.

This proximity sensor is suitable for detecting the vicinity of a possible obstacle on the way of the patient and allows advising the patient of such an obstacle as we will see in the following description.

In this example of FIG. 1 the electronic apparatus 70 is wired linked to the load sensor 40 though a wired connection 44. However, a skilled in the art may easily understand that a wireless communication channel may be provided between the load sensor 40 and the electronic apparatus 70 of the envelope box 60.

Moreover, the electronic apparatus 70 may even be located remotely from the fixation system 1 and the envelope box 60 that may remain just for hosting the flag 61, the speaker 62 and the proximity sensor 63, as will be later disclosed.

In the example of FIG. 2 the skate 20 according to the present disclosure has a base 21 with a curved profile and a thinner orthogonally oriented connection body 22 arranged centrally and extended substantially for the whole length of the base 21. The base 21 is curved with a curvature formed in accordance with requirements of the technology in this sector. The connection body 22 forms a kind of fin and projects from the base 21 of the skate 20 and extends over a length substantially equal to that of the skate 1 itself. The base 21 and the connection body 22 are shape coupled and fixed by means of at least a couple of protruding bumps 26 hosted by corresponding recesses formed The upper profile 23 of this body 22 defines a couple of projecting flanges 24, 25.

The couple of flanges 24, 25 are formed and shaped in the connection body 23 as protruding portions spaced one from the other for interconnecting with a fixation ring, more particularly with the distal foot plate 7.

Each flange has a slot 24a, 25a for regulating the fixation of a connecting member 30 provided for fixing the rail or skate 20 under the foot plate 7. a second end provided with a hole for allowing the connection to the slot 24a or 25a of the flanges 24, 25.

The two slots 24a, 25a have dimensions which are different from each other; more specifically, the slot 24a which is arranged in the front of the skate 20, with respect to the walking direction, has a longitudinal extension smaller than that of the other slot 25a which is arranged at the rear. For example, the longitudinal extension of the front slot 24a is about 13 mm, while the longitudinal extension of the slot 25a at the rear is about 20 mm, in a skate with a length of about 270 mm measured along a flat surface.

In addition, preferably the two protruding portions 24 and 25 are arranged at a different distance from the respective closest end of the skate 20.

More particularly, the projecting member 24, which could be defined as the front part, is placed closer to the front end portion 28 of the skate 1 compared to the distance between the other projecting member 25 and the rear-lying end portion 29 of the skate 20.

In other words, there is a front protruding portions 24 and a rear protruding portions 25, the front protruding portion 24 being placed closer to the front end portion 28 of the skate 20 than the rear protruding portion 25 with respect to the read end portion 29 of the same skate 20.

Essentially, the two protruding portions 24, 25 and consequently the respective slots 24a, 25b, are not arranged symmetrically with respect to a transverse central plane of the skate.

This skate base 21 hosts and supports a couple of load cells 45 representing in this case the load sensor 40. In embodiments of the present disclosure even a single load cell 45 may be enough for the purposes of the present disclosure, for instance just the front load cell.

The load cells 45 are substantially flat and are hosted and protected in cavities 41 defined in the base 21 at the bottom of the skates 20.

Figure 2A:
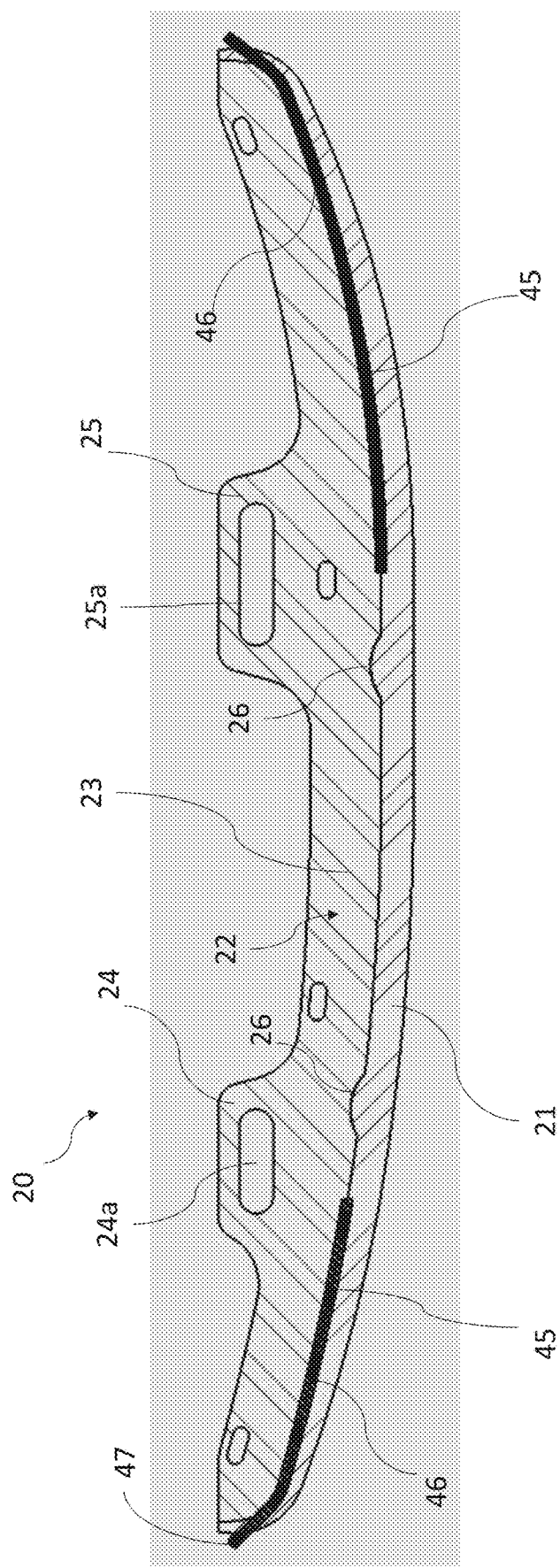
FIG. 2A shows a schematic cross section view of the skate of FIG. 2.

These load cells 45 present thinner flexible element 46 that is extended toward the end portion of the base 21. An extreme end 47 of each flexible element 46 surfaces from the both the end portions of the skate 20, as shown in FIGS. 2 and 2A. In another embodiment of the present disclosure shown in the perspective view of FIG. 2B a removeable cover element 35 is provided to be coupled to the curved base 21 of the skate 20. This cover element 35 is a sort of overshoe of the base portion 21 of the skate 20.

In this respect, the cover element presents opposite rounded portions 34 and 36 wrapping and overlapping the end portions 28 and 29 of the skate 20.

For instance, this cover element 35 may be realized with a material having a rigidity different (e.g., softer or harder) with respect to the material forming the skate 20. This cover element may be realized for instance like a sort of rubber tire.

Moreover, the bottom portion of the cover element 35 abutting the walking surface may be provided with a graven surface or a tread for dampening the impact of the walking steps.

Figure 2B:
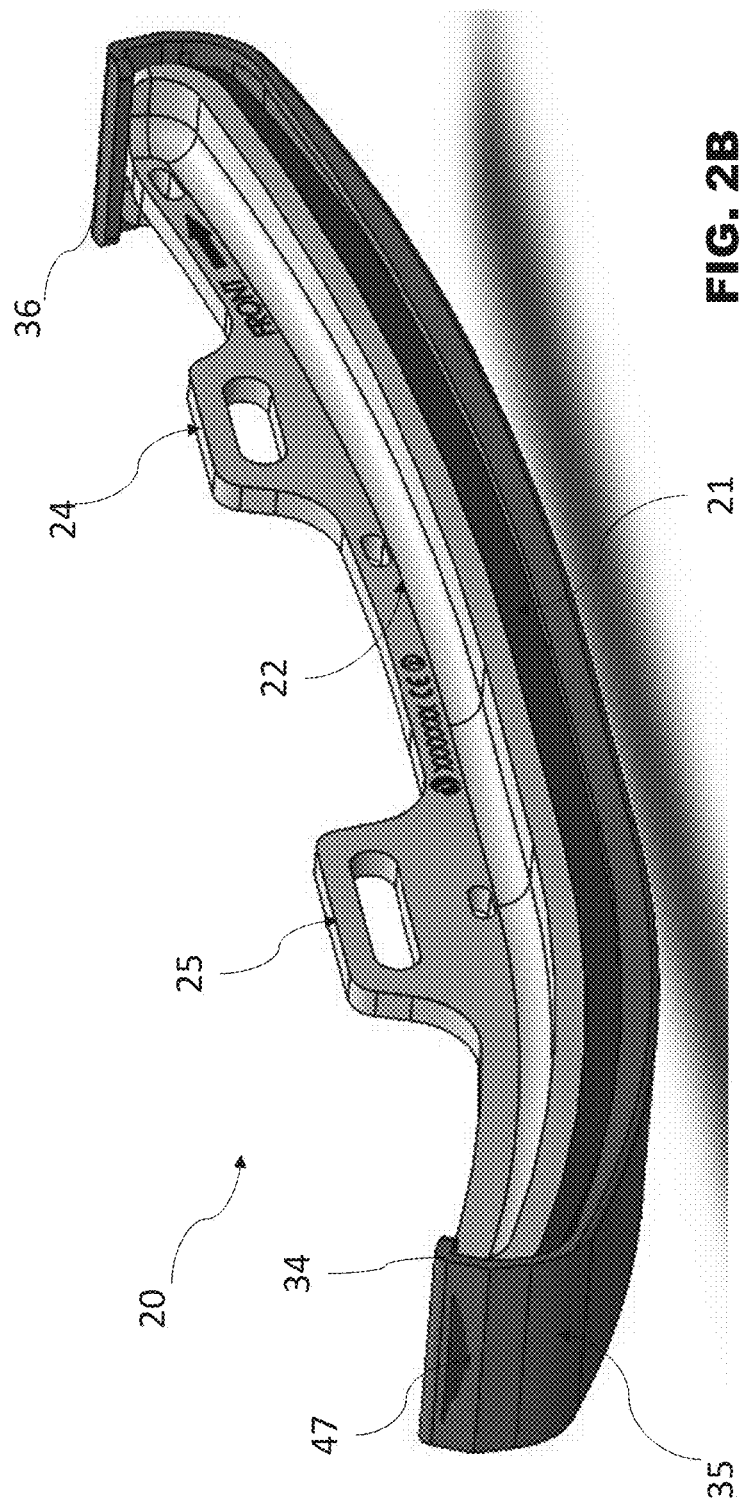
FIG. 2B shows a perspective view of the same skate of FIG. 2A but taken from a different point of view.

If the cover element 35 is used just as an overshoe the extreme end 47 of the flexible element 46 of the load cells surfaces from the opposite end portions of the cover element, as shown in FIG. 2B.

Figure 2C:
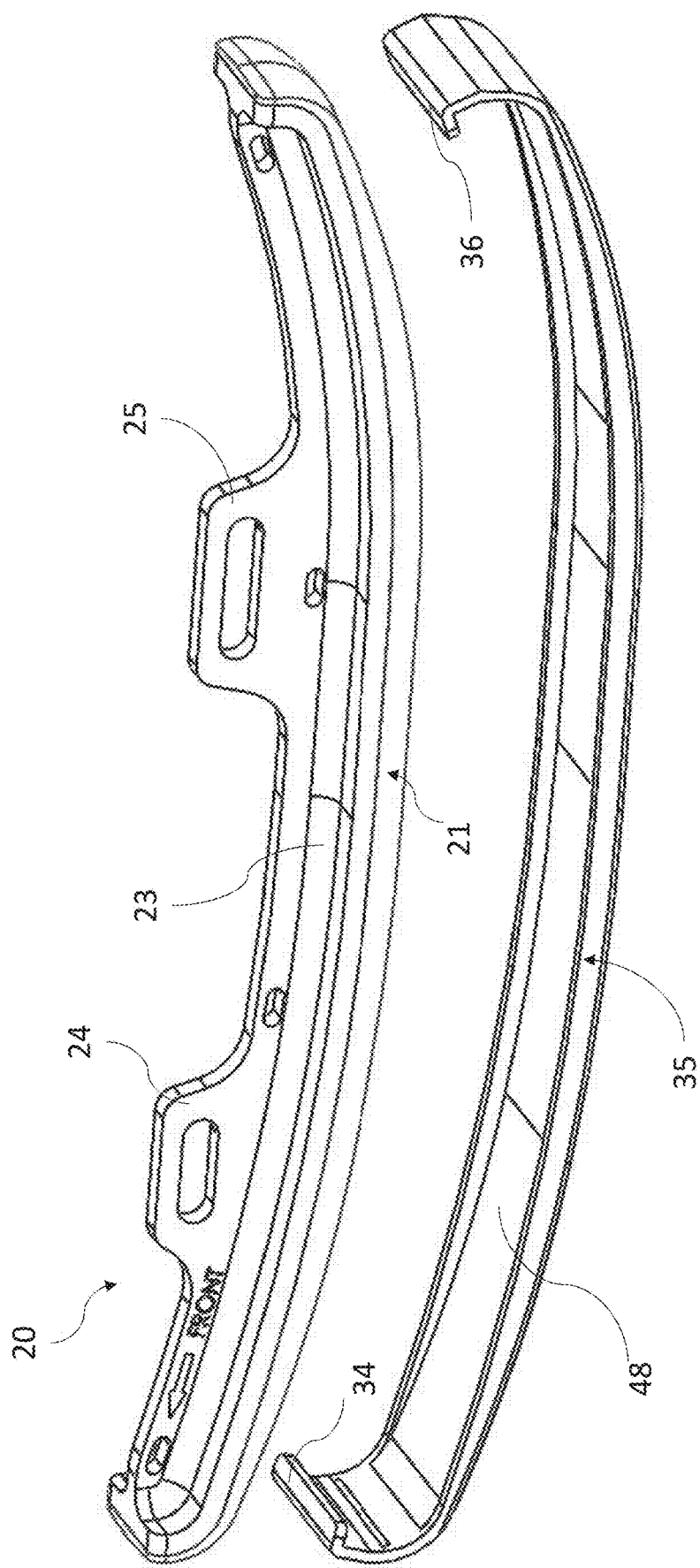
FIG. 2C shows a schematic and perspective view of an alternative embodiment of the skate of the fixation system of the present disclosure.
Figure 2D:
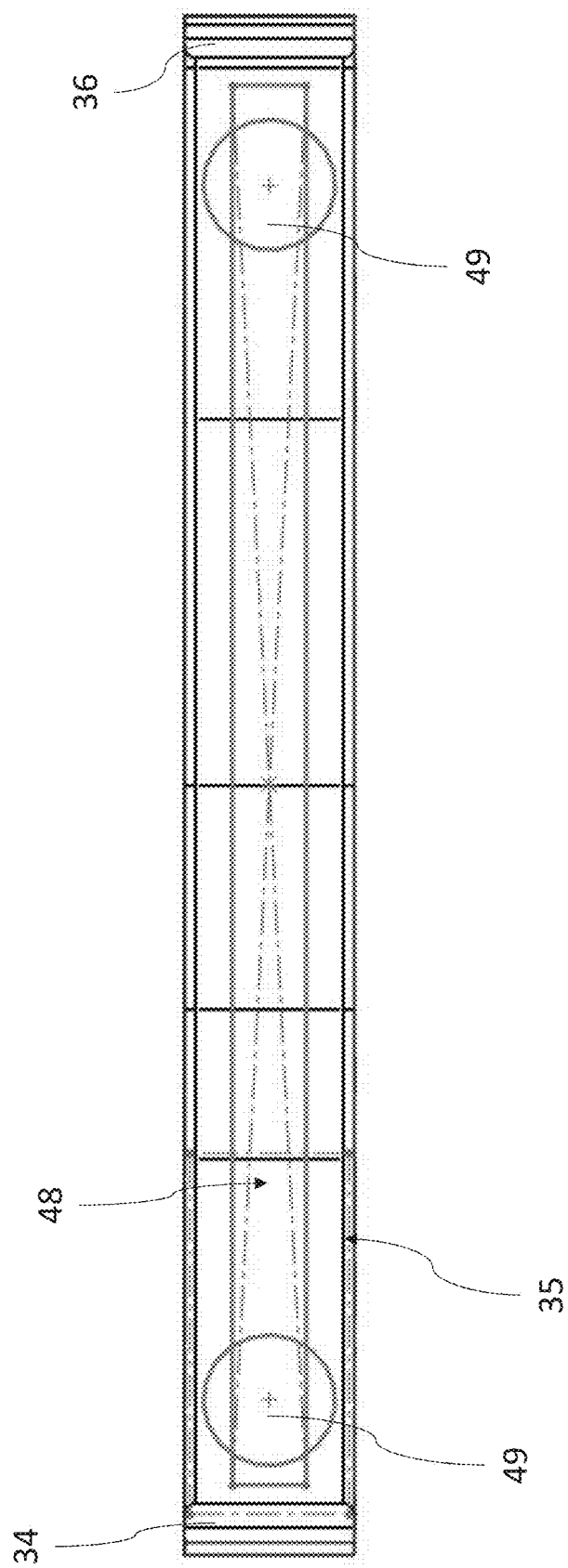
FIG. 2D shows a schematic top view of the alternative embodiment of FIG. 2C including a flexible resistive force sensor.

However, in a different embodiment shown in the example of the FIGS. 2C and 2D, the cover element 35 may host and support a couple of load cells 45 representing the load sensor 40 instead than the base 21 of the skate 20.

In other words, the cover element 35 may be used to host the load cell 45 or an alternative structure of load sensor. In this manner, the load sensors are associated to the removable cover 35 instead than being hidden inside the skate structure.

Even in this embodiment of the present disclosure a single load cell 45 may be enough for the purposes of the present disclosure, for instance just the front load cell.

The load cells 45 hosted by the cover element 35 may be the same previously disclosed with reference to the base 21 of the skate 20. More specifically, those load cells 45 are substantially flat and are hosted and protected in cavities defined in the cover element 35 abutting against the bottom curved profile of the base 21 of the skates 20. Those load cells are kept as in a sandwich between the cover and the base 21.

However, as an alternative solution shown in FIGS. 2C and 2D, the load sensor 40 may be configured as a flexible sensor 48 extended substantially for most of the length of the cover element 35.

This flexible sensor 48 is structured as a strip sensible to resistive force and interconnecting sensing areas 49. A commercial product known as "FlexyForce©" may be used for this purpose.

The flexible sensor 48 is laid down on the surface of the cover element 35 coupled to the bottom profile of the base 21 of the skate 20 while the external surface of the cover element 35 contacts the ground. In this manner the force discharged on the skate 20 is transmitted to the sensor 48 before discharging onto the ground.

The configuration of sensors 45 disclosed with reference to the FIGS. 2 and 2A, or the alternative configuration of the flexible sensor 48 disclosed with reference to the FIGS. 2C and 2D, allows generating a map of the load acting on the surface covered by the sensors to obtain information not only on the quantity but also on the distribution of the load on the surface and on the modality of patient step.

The load sensors 40, 45 or 48 are electrically coupled to an electronic controller 50 that may be either mounted directly onto the system 1 or used as a separate module wirelessly connected to load sensors.

Figure 3:
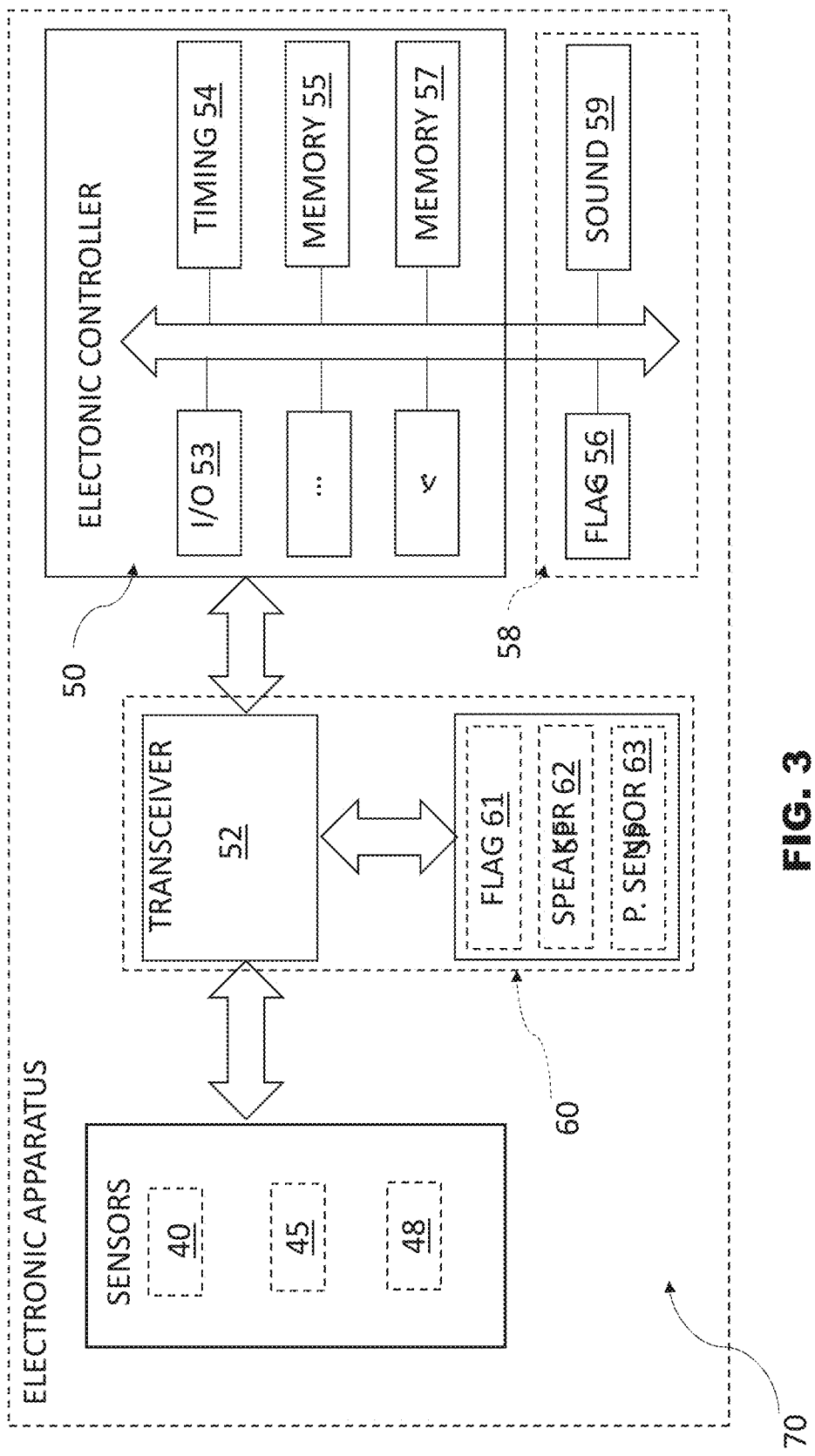
FIG. 3 is a block diagram of an electronic apparatus cooperating with the fixation system of the present disclosure.

In this respect, FIG. 3 shows a block diagram of an electronic apparatus 70 cooperating with the improved orthopaedic external fixation system 1 of the present disclosure.

The electronic apparatus 70 may be considered incorporating an electronic controller 50 and all the electric components allowing the implementation of a method for monitoring the pressure force exerted on a foot or a limb of a patient threated with the orthopaedic external fixation system 1 of the present disclosure.

Moreover, the same electronic apparatus 70 allows monitoring the dynamics of leg loading of a patient and preventing interference with surrounded objects while walking.

Those aims are achieved by a combination of hardware and software components that are disclosed hereinafter.

First of all, electronic apparatus 70 may be considered incorporating one or the other of the sensor components 40, 45 or 48 previously disclosed. According to the previous passages of the present disclosure it is evident that one kind of sensor 40, 45 or 48 may be adopted according to the different embodiment of the fixation system under consideration.

In any case, those sensors 40, 45 or 48 have in common the possibility to generate a sensing signal linked or proportional to the pressure force exerted on a foot or a limb of the patient threated with the fixation system 1.

Such a sensing signal may be an analog or a digital signal but for the purpose of the present disclosure we will take in consideration just digital signals to be elaborated by the electronic controller 50 and we will consider the analog signals as converted on site into digital signals.

Therefore, the load sensors 40 of the first embodiment disclosed in FIG. 1 may be considered equipped with a suitable analog-to-digital converter providing a digital signal corresponding to the analog detection.

The sensing signals detected by the sensors 40, 45 or 48 are transmitted to electronic controller 50 through a transmitter and receiver 52 that is indicated in FIG. 3 as transceiver.

This transceiver 52 may be incorporated into the envelope box 60 mounted on the fixation system 1 or one or both the skates 20. Therefore, the transceiver 52 is in communication with the proximity sensor 63 as well as with the LED flag 61 and the speaker 62.

The transceiver 52 may be considered part of the envelope box 60 or may be considered an independent component associated for instance to the load sensor 40.

The electronic controller 50 may be a structurally independent host device, for instance, a portable device such as a mobile phone or a smartphone, that is in communication with the electronic components of the apparatus 70 on board the fixation system 1. The portable device may be a computer, a server, a laptop computer, a notebook computer, a tablet computer, a mobile phone, a wearable electronic device, a personal electronic device, or a portion or element of such devices.

The electronic controller 50 includes at least the following components: an input/output portion 53, a timing portion 54, a non-volatile memory portion 55, for instance an embedded Flash memory, a volatile memory portion 57, for instance a RAM. Other components are not disclosed being of a conventional type.

The electronic controller 50 is linked to a signaling portions 58 of the portable device, always part of the electronic apparatus 70, including for instance a light flag 56 or a sound emitter 59. The light flag 56 and the sound emitter 59 may be additional or alternative to the flag 61 and speaker 62 of the envelope box 60 on the fixation system 1.

In more details, the electronic controller 50 receives signals from the load sensors 40, 45 or 48 through the transceiver 52 and elaborates such signals according to computer programs stored in the non-volatile memory portion 55.

The electronic controller 50 may elaborate the received signals comparing them with reference signals still stored in the non-volatile memory portion 55.

The electronic controller 50 is coupled to the signaling portion 58 of the electronic apparatus 70 and may issue a flag signal upon detection of a threshold pressure force on said at least one of said rails or skates that overcomes a predetermined reference value stored in the memory portion 55. The flag signal may be a video or audio signal such as a simple light or a warning alarm. This visual signal may be emitted by the led flag 61 or by the flag 56 of the portable device. Similarly, the sound signal may be emitted by the speaker 62 or by the sound emitter 59 of the portable device. Obviously, both the light or sound emitters of the electronic apparatus may be activated by the electronic controller 50.

The electronic apparatus 70 has been disclosed in general terms limited to the understanding of the present disclosure. However, the electronic apparatus 70 may incorporate suitable hardware components comprising at least:
  a power supply battery;
  a microprocessor for data processing;
  volatile and non-volatile memory portions;
  an accelerometer for monitoring movement,
  a pair of interfaces for force sensors,
  an RGB LED light or display;
  a speaker;
  a USB port for IN/OUT data transmission,
  a module for wireless IN/OUT data transmission with Bluetooth and Wi-Fi protocol to external devices such as PCs, smartphones, wearable devices, or other devices with compatible connectivity.

Those components may be hosted inside the envelope 60 or, as previously disclosed, being part of an external accessory attachable to other devices such as a smartphone.

This electronic controller 50 is also equipped with dedicated software (downloadable smartphone application) that allows the processing of digital signals converted by force and movement analog signals. Moreover, the electronic controller 50 is configured for the storage and tracing of data and for handling remote connections with external devices.

The software applications installed on this controller 50 or in a non-volatile memory 55 also permits the surgeon to connect his PC via wireless or USB connection to an electronic unit assigned to the patient and through a dedicated graphic interface and to set a therapeutic protocol defined by configuring certain parameters including amount of load transmitted via the skates on the ground and/or number of steps per day performed by the patient.

More particularly, the software application verifies and confirms that the force and/or movement values transmitted by the sensor(s) falls within a range of force and/or movement values (minimum and maximum) defined by the surgeon. If this condition is not verified, the software sends visual and/or audio feedback via the appropriate interfaces (LED, speaker, smartphone, smartwatch, etc.).

Therefore, the fixator system according to the various embodiments of the present disclosure allows implementing a method for monitoring the pressure force exerted on a foot or a limb of a patient threated with said orthopaedic external fixation system with removable rails or skates; the method comprising the steps of:
- connecting at least a pair of rails or skates to a foot fixation element;
- associating a load sensor to at least one of said rails or skates;
- detecting an electric signal issued by the load sensor;
- elaborating said electric signal in an electronic controller coupled to said load sensor for issuing at least a flag signal upon detection of a threshold pressure force on said at least one of said rails or skates.

The four steps (Step 1, . . . , Step 4) of this method are reported in FIG. 7 as a sort of flow chart diagram.

As alternative, the fixator system according to the various embodiments of the present disclosure allows implementing a method for monitoring the dynamics of leg loading of a patient and preventing interference with surrounded objects while walking; the patient having a foot or a limb threated by said orthopaedic external fixation system with removable rails or skates connected to a foot fixation element; the method comprising:
- associating a load sensor to at least one of said rails or skates;
- detecting an electric signal issued by the load sensor;
- elaborating said electric signal in an electronic controller coupled to said load sensor for issuing at least a flag signal upon detection of a threshold pressure force on said at least one of said rails or skates.

The software incorporated into the controller 50 also stores the data related to the movement and the forces acting on the pads, calculating the frequency of events in which, in the face of feedback from the device, the force and/or movement value read by the sensors has/have remained unchanged (feedback ignored).

This system supports a patient to follow the medical protocol in compliance with signaling when he exceeds, for example, the load to be exercised on the joint, or when the number of daily steps taken is less or greater than that prescribed.

The figures from 4 to 6 shows alternative embodiments of the fixation system of the present disclosure wherein a different combination of load sensors and/or signaling components are provided.

Figure 4:
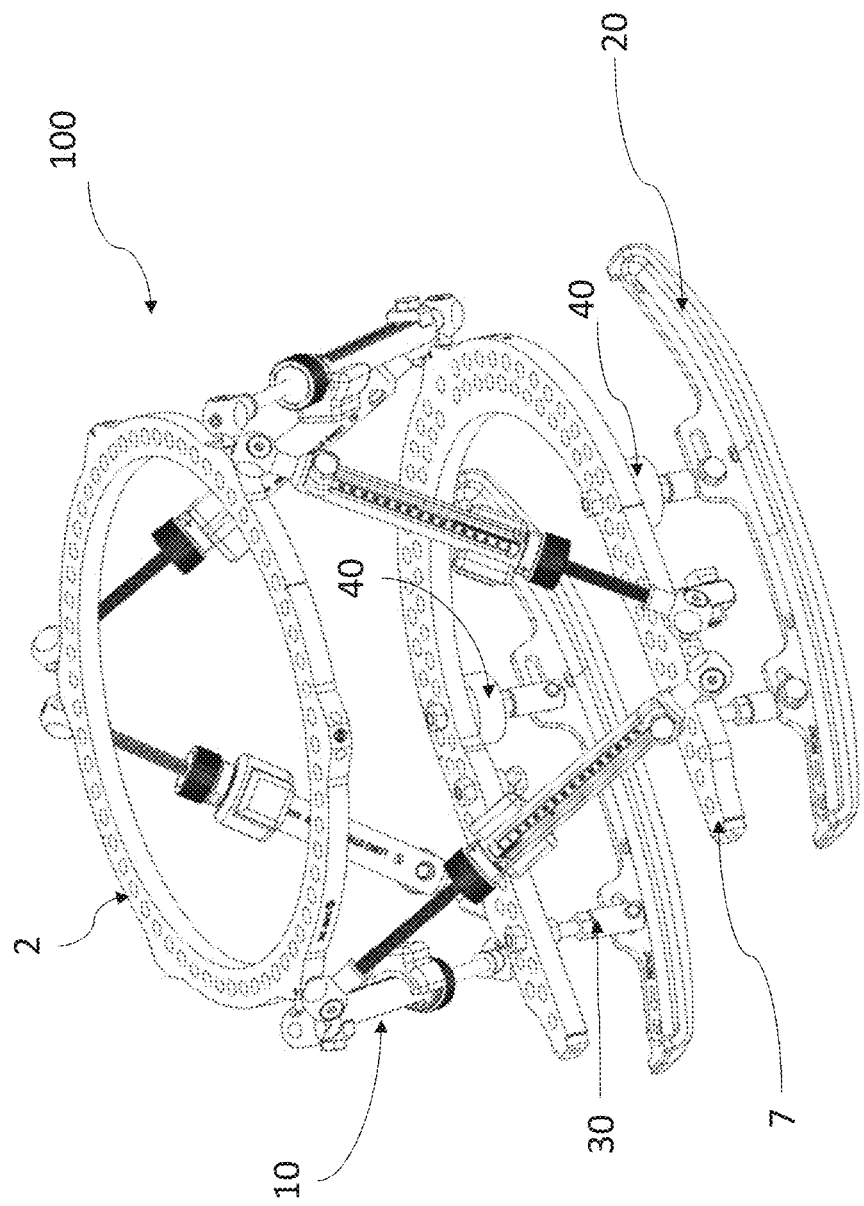
FIG. 4 shows a schematic and perspective view of a further alternative embodiment of an improved orthopaedic external fixation system according to the present disclosure.

For instance, as shown in FIG. 4, and differently from the example of FIG. 1, the disclosed configuration may include a fixation system 100 with two load sensors 40 for each skate 20 resulting in two front sensors and two rear sensors to measure the overall amount of load transmitted to lower limb as well as to compare amount of that load on the lateral and medial sides as well as anterior and posterior sides of the foot during the gait cycle. The two front load sensors may even have a different sensibility if compared to the other rear load sensors, thus allowing to detect if the patient is walking properly or is applying a wrong load on the heel or the front portion of the foot. Each load sensor 40 is associated to connecting member 30 linking the foot plate 7 to the corresponding skates 20.

The configuration of FIG. 4 includes four load sensors 40 (two on each skate 20) but with one load sensor dedicated to the anterior portion of the rail or skate and the other one on the posterior portion of the skate.

This further possible configuration allows to study load distribution on the lateral-anterior, medial-anterior, lateral posterior and medial-posterior areas of the foot during the standing as well as gait cycle. This analysis may include counting of the number of steps with certain proscribed amount of load on the certain areas of the foot.

Furthermore, the system guarantees the possibility for the surgeon to remotely monitor the correct execution of the medical prescription, for example by assessing the ignored feedback, being able to intervene in a timely manner, changing the protocol and/or making contact with the patient for optimize the recovery process.

Figure 5:
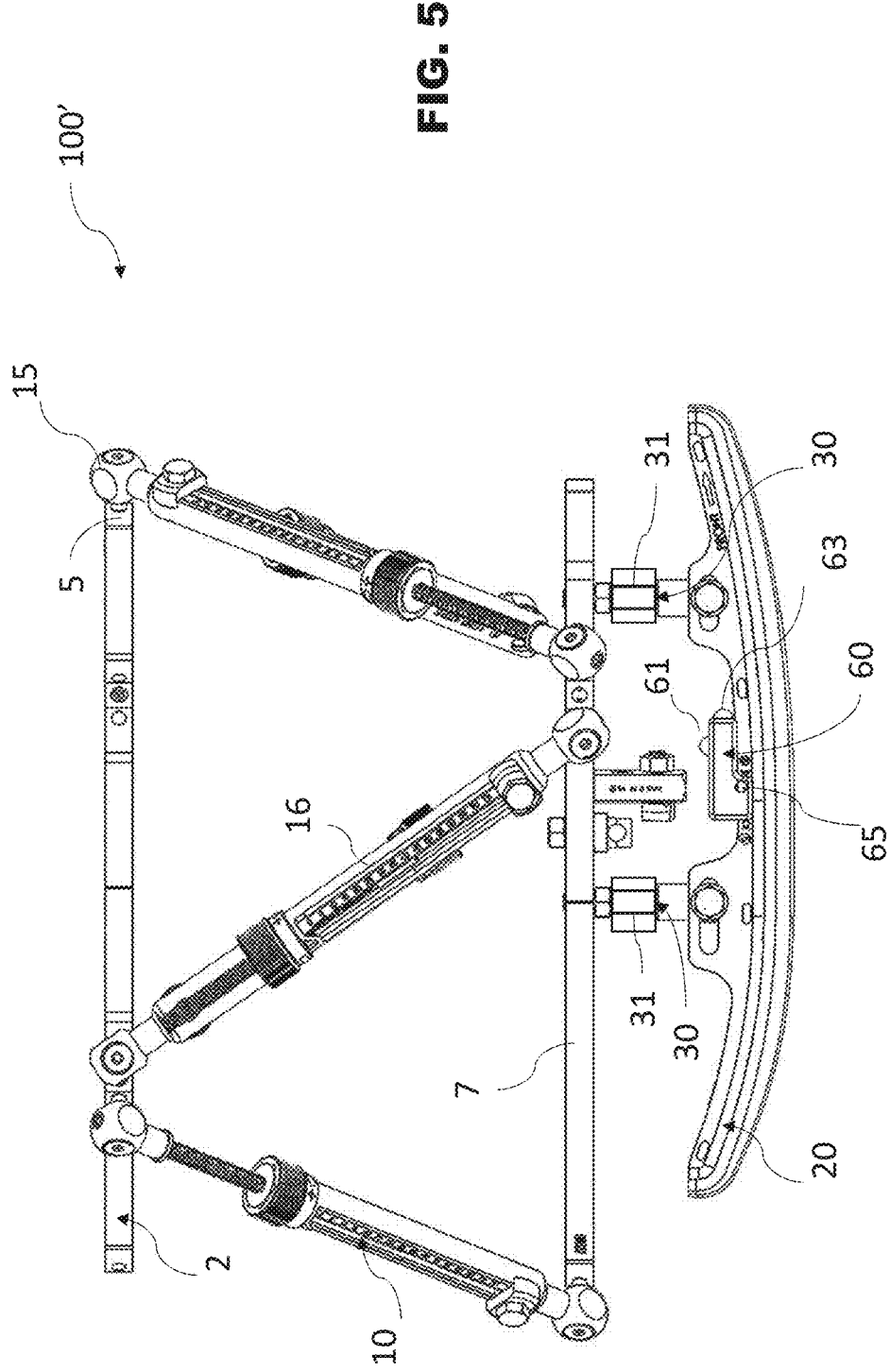
FIG. 5 shows a schematic and lateral view of another alternative embodiment of an improved orthopaedic external fixation system according to the present disclosure.

In another possible configuration, shown in the examples of the FIGS. 5 and 5A, a fixation system 100' of the present disclosure includes the envelope box 60 located in the middle of each skate 20.

Distance measuring sensors 63 (e.g., ultrasound-based sensors or proximity sensors) are attached to the front of the rails allowing to avoid interference (impact) with surrounded objects (e.g., wall) at the certain predetermined distance by sending a visible or hearable signal (e.g., audible signal). This will be beneficial in patients with significantly reduced or absent sensitivity on the foot (e.g., Charcot disease patients).

In addition, similar sensors 65 can be attached on the outside surface of the envelope 60 that is to say at the lateral portion of the rail to produce even better control on surrounding objects.

In another possible configuration, shown in FIG. 6, a fixation system 100" includes a proximity sensors 63 interfaced with small lights 61 at the front of the rails. Those sensors 63 are electrically coupled to the electronic controller 50 and can turn-on those interfaced lights 61 automatically e.g., at dark areas or at dusk. Working as small flashlights, those lights 61 can significantly improve visibility of the objects in the front of the patients again to avoid toes impact with those surrounding objects.

In another possible configuration, the system 100' or 100" includes shock absorbing or damping mechanisms to lessen the impact forces on the bone-wire of bone-pin interface. This may be accomplished by the addition of shock absorbing material, e.g. the cover 35 on the bottom of the rails, while the use of an alternative mechanical components such as central dumping spring 33 disclosed with reference to FIG. 6 (or other dynamization modules located between the rails and the foot plate) would require a particular care to calibrate the response of those elements.

As can be understood from the above description, the system according to the present disclosure may be configured to combine the different embodiments disclosed in the figures and is able to meet the requirements and overcome the drawbacks mentioned above in the introductory part of the present description with reference to the prior art.

It will be understood that embodiments described herein are shown by way of illustration and not as limitations of the invention and can be combined to obtain different possible configurations falling under the scope of the enclosed claims. The principal features of this invention can be employed in various embodiments without departing from the scope of the invention. Those skilled in the art will recognize or be able to ascertain using no more than routine experimentation, numerous equivalents to the specific procedures described herein. Such equivalents are considered within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" or "substantially" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It should be appreciated that the present application provides many applicable inventive concepts that can be embodied in a wide variety of specific contexts. The specific embodiments discussed herein are merely illustrative of specific ways to make and use the fixation device disclosed herein and do not delimit the scope of the application, and their usage does not delimit the application, except as outlined in the claims.

Obviously a person skilled in the art, in order to satisfy any specific requirements which might arise, may make numerous modifications and variations to the invention described above, all of which are contained moreover within the scope of protection of the invention, as defined by the following claims.

The invention claimed is:

1. An improved orthopaedic external fixation system with removable rails or skates comprising:
   at least one distal foot fixation element;
   at least one pair of rails or skates removably connected to said foot fixation element;
   at least one pair of cover elements, each cover element being removably coupled to a base of one rail or skate of the at least one pair of rails or skates;
   at least one load sensor, wherein a cover element of the at least one pair of cover elements couples a load sensor of the at least one load sensor to a rail or skate of the at least one pair of rails or skates, wherein said at least one load sensor is a flexible resistive force sensor for obtaining information on the distribution of the load and is structured as a strip sensible to resistive force with interconnecting sensing areas that extends along a length of the corresponding cover element;
   an electronic apparatus coupled to the at least one load sensor and receiving an electric signal from the at least one load sensor; and
   an electronic controller coupled to said apparatus and issuing at least a flag signal upon detection of a threshold pressure force on said at least one load sensor.

2. The orthopaedic external fixation system of claim 1, wherein said electronic controller is equipped with dedicated software that allows the processing of digital signals converted by force and movement analog signals.

3. The orthopaedic external fixation system of claim 1, wherein said electronic controller is mounted on the system and is equipped with audio and video interfaces.

4. The orthopaedic external fixation system of claim 1, wherein said threshold pressure force has been configured by a surgeon in a memory of said electronic controller according to parameters of the patient.

5. The orthopaedic external fixation system of claim 1, wherein each load sensor of the at least one load sensor includes two load cells with one load cell dedicated to an anterior portion of the corresponding rail or skate and the other one on a posterior portion of the corresponding rail or skate.

6. The orthopaedic external fixation system of claim 5, wherein the cover element of the at least one pair of cover elements has a curved profile and the two load cells are hosted in a cavity formed in said cover element.

7. The orthopaedic external fixation system of claim 1, further including a proximity sensor at a front of a rail or skate of the at least one pair of rails or skates and configured to detect possible interferences with surrounding objects.

8. The orthopaedic external fixation system of claim 1, further including small lights at least at a front of a rail or skate of the at least one pair of rails or skates and configured to be turned on in dark areas or at dusk to light the walking ground.

9. The orthopaedic external fixation system of claim 1, further including distance measuring sensors configured to measure distance to surrounding objects to send a flag signal at certain distances to avoid interference with those surrounded objects.

10. An accessory device for an orthopaedic external fixation system including at least a distal foot fixation element equipped with removeable rails or skates, said device comprising:
    cover elements removably coupled to bases of said rails or skates;
    at least one load sensor, wherein a cover element of the cover elements couples a load sensor of the at least one load sensor to a rail or skate of the rails or skates, wherein said at least one load sensor is a flexible resistive force sensor for obtaining information on the distribution of the load and is structured as a strip sensible to resistive force with interconnecting sensing areas that extends along a length of the corresponding cover element;
    an electronic apparatus coupled to the at least one load sensor and receiving an electric signal from the at least one load sensor; and
    an electronic controller coupled to said apparatus and issuing at least a flag signal upon detection of a threshold pressure force on the corresponding rail or skate of the rails or skates.

11. The accessory device of claim 10, wherein said electronic controller is equipped with dedicated software that allows the processing of digital signals converted by force and movement analog signals.

12. The accessory device of claim 10, wherein said electronic controller is remote to the accessory device and in wireless communication with the accessory device.

13. The accessory device of claim 10, wherein said threshold pressure force has been configured by a surgeon in a memory of said electronic controller according to parameters of the patient.

14. The accessory device of claim 10, wherein said electronic controller is coupled to with audio and video interfaces of the electronic apparatus.

15. The orthopaedic external fixation system of claim 10, further including at least a proximity sensor at a front of a rail or skate of the rails or skates and configured to detect possible interferences with surrounding objects.

16. The orthopaedic external fixation system of claim 10, further including small lights at least at a front of a rail or skate of the rails or skates and configured to be turned on in dark areas or at dusk to light the walking ground.

* * * * *